(12) United States Patent
Cremer et al.

(10) Patent No.: US 7,731,760 B2
(45) Date of Patent: Jun. 8, 2010

(54) OXAZINE DISULFIDE DYES

(75) Inventors: Christian Cremer, Lörrach (DE); Olof Wallquist, Bottmingen (CH)

(73) Assignee: Ciba Corporation, Tarrytown, NY (US)

( * ) Notice: Subject to any disclaimer, the term of this patent is extended or adjusted under 35 U.S.C. 154(b) by 236 days.

(21) Appl. No.: 11/992,878

(22) PCT Filed: Sep. 27, 2006

(86) PCT No.: PCT/EP2006/066784

§ 371 (c)(1),
(2), (4) Date: Mar. 28, 2008

(87) PCT Pub. No.: WO2007/039529

PCT Pub. Date: Apr. 12, 2007

(65) Prior Publication Data

US 2009/0229059 A1    Sep. 17, 2009

(30) Foreign Application Priority Data

Oct. 6, 2005   (EP)  ................................. 05109272

(51) Int. Cl.
*A61Q 5/10* (2006.01)
*C07D 498/02* (2006.01)

(52) U.S. Cl. .................. 8/405; 8/426; 8/465; 8/525; 8/565; 8/570; 8/575; 8/576; 8/587; 132/202; 132/208; 544/101

(58) Field of Classification Search .............. 8/405, 8/426, 465, 525, 565, 570, 575, 576, 587; 132/202, 208; 544/101
See application file for complete search history.

(56) References Cited

U.S. PATENT DOCUMENTS

| | | | | |
|---|---|---|---|---|
| 2,600,690 | A | * 6/1952 | Robbins | 544/75 |
| 4,714,763 | A | 12/1987 | Theodoropulos | 544/31 |
| 5,474,580 | A | 12/1995 | Renfrew et al. | 8/647 |
| 7,015,181 | B2 | 3/2006 | Lambino | 510/141 |
| 2005/0120493 | A1 | 6/2005 | Mockli | 8/405 |

FOREIGN PATENT DOCUMENTS

DE          19750303          5/1999

WO          95/01772          1/1995
WO          95/15144          6/1995

OTHER PUBLICATIONS

STIC Search Report dated Nov. 13, 2009.*
H. Ju et al., Journal of Electroanalytical Chemistry, vol. 518, (2002), pp. 123-130.
T. Higashijima et al., Anal. Chem., vol. 64, (1992), pp. 711-714.
K. Sugawara et al., Journal of Electroanalytical Chemistry, vol. 568, (2004), pp. 7-12.
K. Sugawara et al., Journal of Electroanalytical Chemistry, vol. 536, (2002), pp. 93-96.
English language abstract for DE 19750303, May 20, 1999.

* cited by examiner

*Primary Examiner*—Eisa B Elhilo
(74) *Attorney, Agent, or Firm*—Mervin G. Wood

(57) ABSTRACT

Disclosed are certain oxazine disulfide dyes useful for the dyeing of organic materials, such as keratin fibers, preferably human hair. the dyes are for instance of the formulae 14 Claims, No Drawings

OXAZINE DISULFIDE DYES

The present invention relates to novel oxazine disulfide dyes, compositions thereof and to their use for the dyeing of organic materials, such as keratin fibers, wool, leather, silk, cellulose or polyamides, especially keratin-containing fibers, cotton or nylon, and preferably hair, more preferably human hair.

It is known, for example, from WO 95/01772 that cationic dyes can be used for the dyeing of organic material, for example keratin, silk, cellulose or cellulose derivatives, and also synthetic fibers, for example polyamides. Cationic dyes exhibit very brilliant shades. A disadvantage is their unsatisfactory fastness to washing.

The technical problem is to provide dyes that are distinguished by deep dyeing having good fastness properties with respect to washing, light, shampooing and rubbing.

Accordingly, the present invention relates to compounds of formula Compounds of formula

wherein

A is hydrogen; or a radical of formula (1a) *—S—$Y_2$—$(Z_2)_r$-$D_2$;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—$(CH_2)_p$—C(O)—**; *—$(CH_2CH_2$—O$)_s$—**; *—$(CH_2)_p$—C(O)O—**; *—$(CH_2)_p$—OCO—**; *—$(CH_2)_p$—N($R_1$)—**;

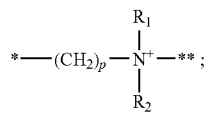

*—$(CH_2)_p$—CON($R_1$)—**; *—$(CH_2)_p$—($R_1$)NC(O)—**; —O—; —S—; —S(O)—; —S(O)$_2$—; or a cationic biradical of a substituted or unsubstituted aromatic or heteroaromatic compound of the formula

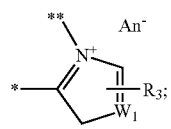

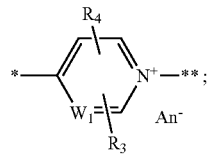

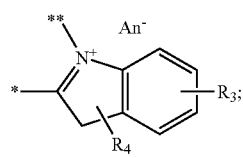

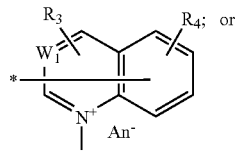

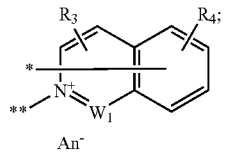

wherein the asterix * indicates the linkage to $D_1$ and/or $D_2$;

the asterix ** indicates the linkage to $Y_1$ and/or $Y_2$;

$W_1$ is N or a radical of $CR_5$;

$R_1$, $R_2$, $R_3$, $R_4$ and $R_5$ independently from each other are hydrogen; $C_1$-$C_{14}$alkyl; $C_2$-$C_{14}$alkenyl; $C_5$-$C_{10}$aryl; $C_5$-$C_{10}$aryl-($C_1$-$C_{10}$alkyl); or —$C_1$-$C_{10}$alkyl($C_5$-$C_{10}$aryl);

$D_1$ and $D_2$ independently from each other ar the residue of an organic dye selected from the radical of formula

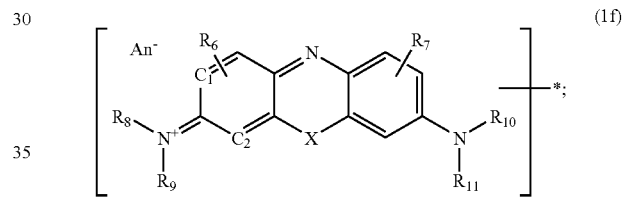

$R_6$ and $R_7$ independently from each other are hydrogen; $C_1$-$C_{20}$alkyl; $C_1$-$C_{20}$alkoxy; $C_3$-$C_6$cycloalkyl; $C_5$-$C_{10}$aryl; anellated aromatic groups; carboxylate; or sulfonate groups;

$R_8$, $R_9$ and $R_{10}$, $R_{11}$ and $R_{12}$ each independently from each other are hydrogen; unsubstituted or substituted, straight-chain or branched, monocyclic or polycyclic, interrupted or uninterrupted $C_1$-$C_{14}$alkyl, $C_2$-$C_{14}$alkenyl, $C_6$-$C_{10}$aryl, $C_6$-$C_{10}$aryl-$C_1$-$C_{10}$alkyl or $C_5$-$C_{10}$alkyl($C_5$-$C_{10}$aryl); or $R_8$ and $R_9$ or $R_{10}$ and $R_{11}$ together with the linking nitrogen atom form a 5 to 7 membered carbocyclic ring which may contain one or more than one hetero atom; or $R_8$ is linked to $C_1$ together with $N^+$ forming a 5-7 membered carbocyclic ring; or $R_9$ is linked to $C_2$ together with $N^+$ forming a 5-7 membered carbocyclic ring;

X is —O—; or —N($R_9$)—; or —S—;

p is a number from 0 to 5;

r is 0 or 1; and s is a number from 1 to 5.

$C_1$-$C_{12}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl.

$C_1$-$C_{12}$alkylene is for example methylene, ethylene, propylene, isopropylene, n-butylene, sec-butylene, tert-butylene, n-pentylene, 2-pentylene, 3-pentylene or 2,2'-dimethylpropylene, n-hexylene, n-octylene, 1,1',3,3'-tetramethylbutylene, 2-ethylhexylene, nonylene, decylene, undecylene or dodecylene.

Alkylene may be straight-chain, branched, or, from $C_5$alkyl upwards, monocyclic or polycyclic, and may be interrupted by hetero atoms, such as such as O, S, —CO—, N, NH, $NR_{54}$, —OCO—, —CO(OR$_4$)—, —CONR$_4$—, —($R_5$)NC(O)—; for example $C_1$-$C_{10}$alkylene may be a reissue such as: —CH$_2$CH$_2$—O—CH$_2$CH$_2$—O—CH$_2$CH$_2$—, —CH$_2$CH$_2$—O—CH$_2$CH$_2$—, —CH$_2$CH$_2$—O—CH$_2$—, —CH$_2$—O—CH$_2$—, —CH$_2$CH$_2$—CH$_2$CH$_2$—O—CH$_2$CH$_2$—, —CH$_2$CH$_2$—CH(N(CH$_3$)$_2$)—CH$_2$—CH$_2$—, CH$_2$—NH$_2$—CH$_2$—CH$_2$, —CH$_2$CH$_2$—NH—CH$_2$CH$_2$—, —CH$_2$CH$_2$—NCH$_3$—CH$_2$CH$_2$—, —CO—CH$_2$—, —CH$_2$CO—, —CH$_2$CH$_2$—NHCO—CH$_2$CH$_2$—, —CH$_2$CH$_2$—CONH—CH$_3$—CH$_2$CH$_2$—, —CH$_2$CH$_2$—NCH$_3$CO—CH$_2$CH$_2$—, —CH$_2$CH$_2$—CONCH$_3$—CH$_3$—CH$_2$CH$_2$—, —CH$_2$—NHCO—CH$_2$CH$_2$—, or —CH$_2$CH$_2$—NHCO—CH$_2$—, —CH$_2$CH$_2$—CONH—CH$_2$— or —CH$_2$—CONH—CH$_2$CH$_2$—.

$C_5$-$C_{10}$cycloalkylene is for example cyclopentylene, cyclohexylene, cycloheptylene, cyclooctylene, cyclononylene or cyclodecylene.

$C_5$-$C_{10}$arylene is for example phenylene or naphthylene.

Aryl-alkylene is for example $C_5$-$C_{10}$aryl-$C_1$-$C_{10}$alkylene.

Alkyl-arylene is for example $C_1$-$C_{10}$alkyl-$C_5$-$C_{10}$arylene.

Preferred are compounds of formula (1) wherein $Y_1$ and $Y_2$ are $C_5$-$C_{10}$cycloalkylene; or $C_1$-$C_{10}$alkylene; and more preferably wherein $Y_1$ and $Y_2$ are $C_1$-$C_5$alkylene.

Furthermore compounds of formula (1) are preferred, wherein $Z_1$ and $Z_2$ independently from each other are —CO—; *—CH$_2$—CO—NH—**; *—(CH$_2$)$_3$—N$^+$(CH$_3$)(CH$_3$)—; or —(CO)—O—*.

Preferably in formula (1f)

$R_7$ and $R_8$ or $R_9$ and $R_{10}$ together with the linking nitrogen atom form a piperidine ring of formula

(1b)

wherein the asterix (*) is directed to $Z_1$ or $Z_2$ respectively; and the asterices (**) are directed to the linking nitrogen atom of $R_1/R_2$ or $R_3/R_4$ respectively.

Most preferred are compounds of formula (1), wherein n is 2.; and even more preferred are compounds of formula (1), wherein $D_1$ is identical to $D_2$;

$Y_1$ is identical to $Y_2$;

$Z_1$ is identical to $Z_2$;

p is 0; or 1; and q and r are each 1.

Examples for the compounds according to the present invention are listed in Table 1 below:

(2)

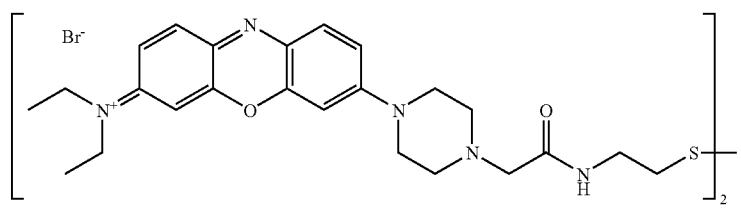

(3)

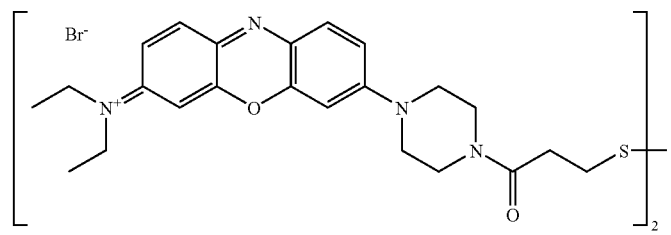

(4)

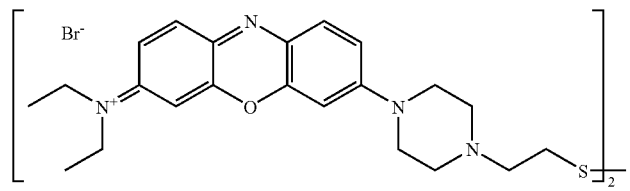

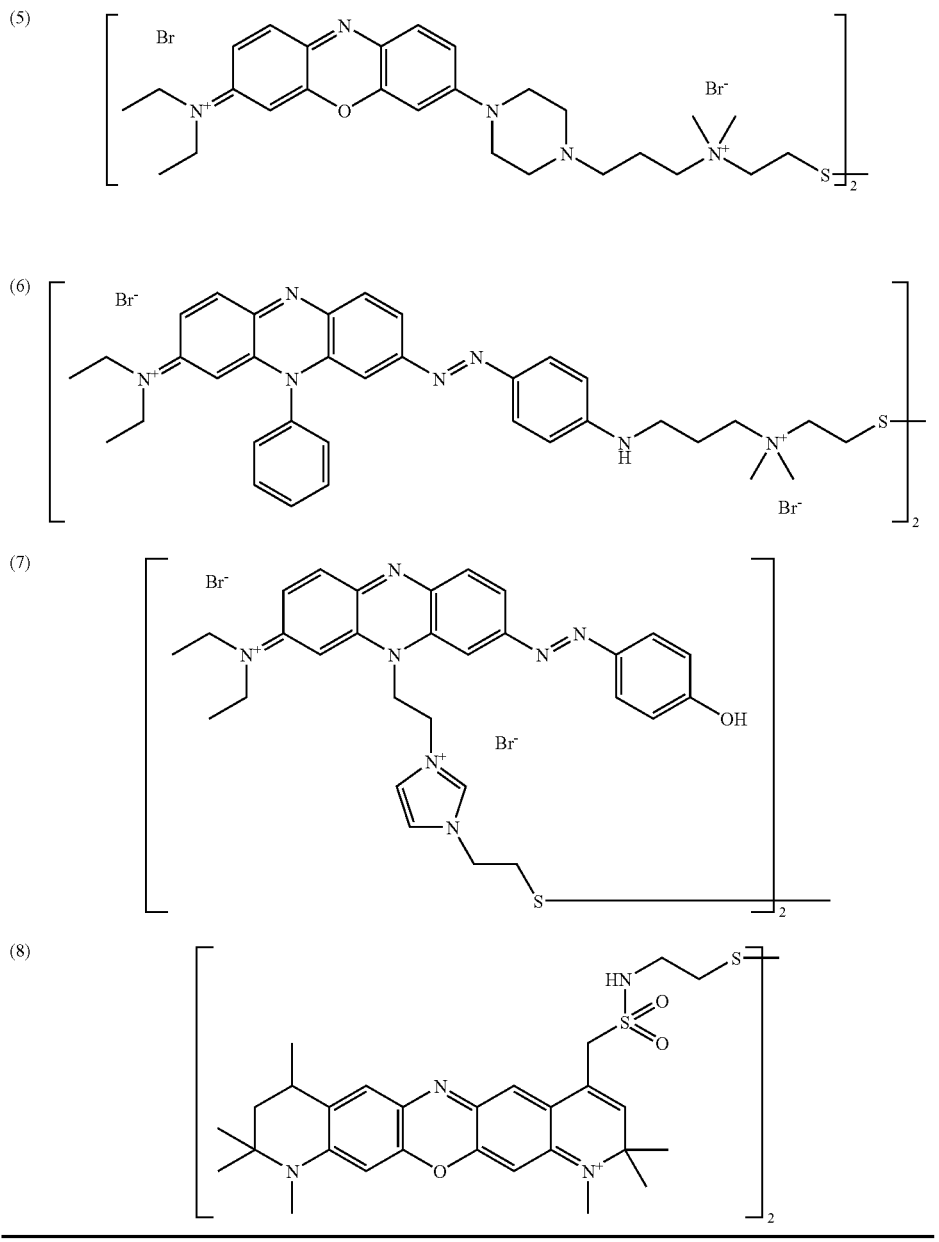

A further embodiment of the present invention relates to processes for the preparation of the dyes of formula (1).

Generally, the process comprises reacting 2 mol of the compound of formula (1h) $D_1$-H with the compound of formula (1i) *-[S—$Y_1$—($Z_1$)$_r$-Hal]$_2$ to give the compound of formula (1k) [$D_1$-($Z_1$)$_r$—$Y_1$—S-]$_2$*.

The dyes according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties for example to washing, fastness to light, shampooing and rubbing. The stabilities, in particular the storage stability of the dyes and the dyes in formulations according to the invention are excellent.

Generally, hair dyeing agents on a synthetic base may be classified into three groups:
temporary dyeing agents
semipermanent dyeing agents, and
permanent dyeing agents.

The multiplicity of shades of the dyes can be increased by combination with other dyes.

Therefore the dyes of formula (1) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1) may be used in combination with at least one single direct dye different from the dyes of formula (1).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäsches Inventar der Kosmetikrohstoffe", 1996, published by The European Commission, obtainable in diskette form from the Bundesverband der deutschen Industrie-und Handelsunternehmen fur Arzneimittel, Reformwaren und Körperpflegemittel e.V., Mannheim.

More preferred direct dyes which are useful for the combination with at least one single dye of formula (1), especially for semi permanent dyeing, are: 2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3-yl)-azo)pyridine, 2-nitro-5-glyceryl-methylaniline, 3-methylamino-4-nitro-phenoxyethanol, 4-amino-2-nitrodiphenyleneamine-2'-carboxylic acid, 6-nitro-1,2,3,4,-tetrahydroquinoxaline, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethyl-aminophenol, 4-amino-3-nitrophenol, 4-hydroxypropylamine-3-nitrophenol, hydroxyanthrylaminopropylmethyl morpholino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the dyes of formula (1) may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6 (compound of formula 106); or the cationic dye of formula (3) as described in EP-A-714,954, or with a yellow cationic dye of formula

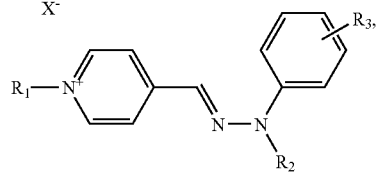

(DD1)

wherein $R_1$ and $R_2$ are each independently of the other a $C_1$-$C_8$alkyl; or an unsubstituted or substituted benzyl;

$R_3$ is hydrogen; $C_1$-$C_8$alkyl; $C_1$-$C_8$alkoxy; cyanide; or halide; preferably hydrogen; and $X^-$ is an anion; and preferably a compound of formula (DD1), wherein $R_1$ is methyl; $R_2$ is benzyl; $R_3$ is hydrogen; and $X^-$ is an anion; or wherein $R_1$ is benzyl; $R_2$ is benzyl; $R_3$ is hydrogen; and $X^-$ is an anion; or wherein $R_1$ is benzyl; $R_2$ is methyl; $R_3$ is hydrogen; and $X^-$ is an anion.

Furthermore, cationic nitroaniline and anthraquinone dyes are useful for a combination with a dye of formula (1), for example the dyes as described in the following patent specifications: U.S. Pat. No. 5,298,029, especially in col 2, l. 33 to col 5, l. 38; U.S. Pat. No. 5,360,930, especially in col 2, l. 38 to col 5, l. 49; U.S. Pat. No. 5,169,403, especially in col 2, l. 30 to col 5, l. 38; U.S. Pat. No. 5,256,823, especially in col 4, l. 23 to col 5, l. 15; U.S. Pat. No. 5,135,543, especially in col 4, l. 24 to col 5, l. 16; EP-A-818 193, especially on p. 2, l. 40 to p. 3, l. 26; U.S. Pat. No. 5,486,629, especially in col 2, l. 34 to col 5, l. 29; and EP-A-758 547, especially on p. 7, l. 48 to p. 8, l. 19.

The dyes of formula (1) may also be combined with acid dyes, for example the dyes which are known from the international names (Color index), or trade names.

Preferred acid dyes which are useful for the combination with a dye of formula (1) are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The dyes of formula (1) according to the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The dyes of formula (1) may also be combined with uncharged dyes, for example selected from the group of the nitroanilines, nitrophenylenediamines, nitroaminophenols, anthraquinones indophenols, phenazines, phenothiazines, bispyrazolons, bispyrazol aza derivatives and methines.

Furthermore, the dyes of formula (1) may also be used in combination with oxidation dye systems.

Oxidation dyes, which, in the initial state, are not dyes but dye precursors are classified according to their chemical properties into developer and coupler compounds.

Suitable oxidation dyes are described for example in

DE 19 959 479, especially in col 2, l. 6 to col 3, l. 11;

"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p., 2 l. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluoylendiamine, p-, m- o-aminophenol, N,N-bis-(2-hydroxyethyl)-p-phenylenediamine sulfate, 2-amino-4-hydroxy-ethylaminoanisole sulfate, hydroxyethyl-3,4-methylenedioxyaniline, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

The dyes of formula (1) may also be used together with unsaturated aldehydes as disclosed in DE 19 717 224 (p. 2, l. 50 to l. 66 and on p. 3 l. 8 to l. 12) which may be used as direct dyes or, alternatively together with oxidation dye precursors.

Further preferred for a combination with a dye of formula (1) are the following oxidation dye precursors:

the developer/-coupler combination 2,4,5,6-tetraminopyrimidine and 2-methylresorcine for assessing of red shades;

p-toluenediamine and 4-amino-2-hydroxytoluene for assessing of blue-violet shades;

p-toluenediamine and 2-amino-4-hydroxyethylaminoanisole for assessing of blue shades;

p-toluenediamine and 2,4-diamino-phenoxyethynol for assessing of blue shades;

methyl-4-aminophenol and 4-amino-2-hydroxytoluene for assessing of orange shades;

p-toluenediamine and resorcine for assessing of brown-green shades;

p-toluenediamine and 1-naphthol for assessing of blue-violet shades, or p-toluenediamine and 2-methylresorcine for assessing of brown-gold shades.

Furthermore, autooxidizable compounds may be used in combination with the dyes of formula (1).

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indol, or indoline, especially 5,6-dihydroxyindol or 5,6-dihydroxyindoline derivatives as described in WO 99/20234, especially on p. 26, l. 10 to p. 28, l. 15, or in WO 00/28957 on p. 2, third paragraph.

Preferred autooxidizable benzene derivatives are 1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylaminophenol, 2,6-diamino-1,4-dihydroxy-benzene, and the salts of these compounds, which are accessible with acid.

Preferred autooxidizable indol derivatives are 5,6-dihydroxyindol, 2-methyl-5,6-dihydroxy-indol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroixyindol, 5,6-diacetoxyindol, acid of 5,6-dihydroxyindol-2-carbon acid, and the salts of these compounds, which are accessible with acid.

The dyes of formula (1) may also be used in combination with naturally occurring dyes, such as henna red, henna neutral, henna black, camomile blossom, sandalwood, black tea, Rhamnus frangula bark, sage, campeche wood, madder root, catechu, sedre and alkanet root. Such dyeings are described, for example, in EP-A-404 868, especially on p. 3, l. 55 to p. 4, l. 9.

Furthermore, the dyes of formula (1) may also be used in combination with capped diazotised compounds.

Suitable diazotised compounds are for example the compounds of formulae (1)-(4) in WO 2004/019897 (bridging pages 1 and 2) and the corresponding watersoluble coupling components (I)-(IV) as disclosed in the same reference.

Further preferred dyes or dye combinations which are useful for the combination with a dye of formula (1) according to the present invention are described in (DC-01): WO 95/01772, wherein mixtures of at least two cationic dyes are disclosed, especially p. 2, I. 7 to p. 4, I. 1, preferably p. 4, I. 35 to p. 8, I. 21; formulations p. 11, last§-p. 28, I. 19;

(DC-02): U.S. Pat. No. 6,843,256, wherein cationic dyes are disclosed, especially the compounds of formulae (1), (2), (3) and (4) (col. 1, I. 27-col. 3, I. 20, and preferably the compounds as prepared in the examples 1 to 4 (col. 10, I. 42 to col. 13, I. 37; formulations col. 13, I. 38 to col. 15, I. 8;

(DC-03): EP 970 685, wherein direct dyes are described, especially p. 2, I. 44 to p. 9, I. 56 and preferably p. 9, I. 58 to p. 48, I. 12; processes for dyeing of keratin-containing fibers especially p. 50, I. 15 to 43; formulations p. 50, i. 46 to p. 51, I. 40;

(DC-04): DE-A-19 713 698, wherein direct dyes are described, especially p. 2, I. 61 to p. 3, I. 43; formulations p. 5, I. 26 to 60;

(DC-05): U.S. Pat. No. 6,368,360, wherein directed dyes (col. 4, I. 1 to col. 6, I. 31) and oxidizing agents (col. 6, I. 37-39) are disclosed; formulations col. 7, I. 47 to col. 9, I. 4;

(DC-06): EP 1 166 752, wherein cationic dyes (p. 3, I. 22-p. 4, I. 15) and anionic UV-absorbers (p. 4, I. 27-30) are disclosed; formulations p. 7, I. 50-p. 9, I. 56;

(DC-07): EP 998,908, wherein oxidation dyeings comprising a cationic direct dye and pyrazolo-[1,5-a]-pyrimidines (p. 2, I. 48-p. 4, I. 1) are disclosed; dyeing formulations p. 47, I. 25 to p. 50, I. 29;

(DC-08): FR-2788432, wherein combinations of cationic dyes with Arianors are disclosed, especially p. 53, I. 1 to p. 63, I. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianoren and/or oxidative dyes, especially p. 2, I. 16 to p. 3, I. 16; dyeing formulations on p. 53, I. 1 to p. 63, I. 23;

(DC-09): DE-A-19 713 698, wherein the combinations of direct dyes and permanent-wave fixing comprising an oxidation agent, an oxidation dye and a direct dye are disclosed; especially p. 4, I. 65 to p. 5, I. 59;

(DC-10): EP 850 638, wherein developer compounds and oxidizing agents are disclosed; especially p. 2, I. 27 to p. 7, I. 46 and preferably p. 7, I. 20 to p. 9, I. 26; dyeing formulations p. 2, I. 3-12 and I. 30 to p. 14, and p. 28, I. 35-p. 30, I. 20; preferably p. 30, I. 25-p. 32, I. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, I. 40-col. 7, I. 14), optionally dispersed in an organic pulverulent excipient and/or a mineral pulverulent excipient, and a composition (C) containing one or more oxidizing agents are disclosed; formulations col. 8, I. 60-col. 9, I. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, I. 17-col. 13, I. 65; dyeing formulations in col. 2, I. 16 to col. 25, I. 55, a multi-compartment dyeing device is described in col. 26, I, 13-24;

(DC-13): WO 99/20235, wherein compositions of at least one cationic dye and at least one nitrated benzene dye with cationic direct dyes and nitro benzene direct dyes are described; on p. 2, I. 1 to p. 7, I. 9, and p. 39, I. 1 to p. 40 I. 11, preferably p. 8, I. 12 to p. 25 I. 6, p. 26, I. 7 to p. 30, I. 15; p. 1, I. 25 to p. 8, I. 5, p. 30, I. 17 to p. 34 I. 25, p. 8, I. 12 to p. 25 I. 6, p. 35, I. 21 to 27, especially on p. 36, I. 1 to p. 37;

(DC-14): WO 99/20234, wherein compositions comprising at least one direct cationic dye and at least one autooxidisable dye, especially benzene, indol and indoline derivatives are described, preferably direct dyes on p. 2, I. 19 to p. 26, I. 4, and autooxidisable dyes as disclosed especially on p. 26, I. 10 to p. 28, I. 15; dyeing formulations especially on p. 34, I. 5 to p. 35, Ii 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, I. 41 to p. 7, I. 52, dyeing formulations p. 19, I. 50-p. 22, I. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, I. 50 to p. 8, I. 44 are disclosed; dyeing formulations p. 21, I. 30-p. 22, I. 57;

(DC-17): WO 99/48856, wherein oxidation dyeing compositions comprising cationic couplers are disclosed, especially p. 9, I. 16-p. 13, I. 8, and p. 11, I. 20-p. 12, I. 13; dyeing formulations p. 36, I. 7-p. 39, I. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptids, aromatic hydroxy compounds, and/or at least one CH-active compound are disclosed p. 3, I. 42-p. 5 I. 25; dyeing formulations p. 8, I. 25-p. 9, I. 61.

In the dye combinations disclosed in the references (DC-01-DC-18) above, the dyes of formula (1) according to the present invention may be added to the dye combinations or dyeing formulations or may be replaced with at least one dye of formula (1).

The present invention also relates to formulations, which are used for the dyeing of organic materials, preferably keratin-containing fibers, and most preferably human hair, comprising at least one dye of formula (1).

Preferably the dyes of formula (1) are incorporated into the composition for treating organic material, preferably for dyeing in amounts of 0.001-5% b.w. (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

The pH value of the ready-to-use dyeing compositions is usually from 2 to 11, preferably from 5 to 10.

Preferably the dyeing compositions, which are not stable to reduction, are prepared with oxidizing agent free compositions just before the dyeing process.

One preferred embodiment of the present invention relates to the formulation of dyes, wherein the dyes of formula (1) are in powder form.

Powder formulations are preferably used if stability and/or solubility problems as for example described in DE 197 13 698, p. 2, I. 26 to 54 and p. 3, I. 51 to p. 4, I. 25, and p. 4, I. 41 to p. 5 I. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for per-manent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts, for example emulsifiers may be present in the dyeing compositions in concentrations from 0.5 to 30% b.w. and thickeners in concentrations from 0.1 to 25% b.w. of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

A shampoo has, for example, the following composition:
0.01 to 5% b.w. of a dye of formula (1);
8% b.w of disodium PEG-5 laurylcitrate Sulfosuccinate, Sodium Laureth Sulfate;
20% b.w. of sodium cocoamphoacetate;
0.5% b.w. of methoxy PEG/PPG-7/3 aminopropyl dimethicone;
0.3% b.w. of hydroxypropyl guar hydroxypropytrimonium chloride;
2.5% b.w. of PEG-200 hydrogenated glyceryl palmate; PEG-7 glyceryl cocoate;
0.5% b.w. of PEG-150 distearate;
2.2. % b.w of citric acid;
perfume, preservatives; and
water ad 100%.

The dyes of formula (1) may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

The dyeing compositions according to the invention may comprise any active ingredients, additives or adjuvants known for such preparations, like surfactants, solvents, bases, acids, perfumes, polymeric adjuvants, thickeners and light stabilisers.

The following adjauvents are preferably used in the hair dyeing compositions of the present invention:
non-ionic polymers, for example vinylpyrrolidone/vinyl acrylate copolymers, polyvinyl-pyrrolidone and vinylpyrrolidone/vinyl acetate copolymers and polysiloxanes;
cationic polymers, such as quaternised cellulose ethers, polysiloxanes having quaternary groups, dimethyldiallylammonium chloride polymers, copolymers of dimethyldiallyl-ammonium chloride and acrylic acid, as available commercially under the name Merquat® 280 and the use thereof in hair dyeing as described, for example, in DE-A-4 421 031, especially p. 2, I. 20 to 49, or EP-A-953 334;
acrylamide/dimethyldiallylammonium chloride copolymers, diethyl-sulfate-quaternised dimethylaminoethyl methacrylate/vinylpyrrolidone copolymers, vinylpyrrolidone/-imidazolinium methochloride copolymers;
quaternised polyvinyl alcohol:
zwitterionic and amphoteric polymers, such as acrylamido-propyltrimethylammonium chloride/acrylate copolymers and octylacrylamide/methyl methacrylate/tert-butylaminoethyl methacrylate/2-hydroxypropyl methacrylate copolymers;
anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;
thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;
structuring agents, such as glucose and maleic acid;
hair-conditioning compounds, such as phospholipids, for example soya lecithin, egg lecithin, cephalins, silicone oils, and conditioning compounds, such as those described in DE-A-19 729 080, especially p. 2, I. 20 to 49, EP-A-834 303, especially p. 2, I. 18-p. 3, I. 2, or EP-A-312 343, especially p. 2, I. 59-p. 3, I. 11;
protein hydrolysates, especially elastin, collagen, keratin, milk protein, soya protein and wheat protein hydrolysates, condensation products thereof with fatty acids and also quaternised protein hydrolysates;

perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, substances for adjusting the pH value;

panthenol, pantothenic acid, allantoin, pyrrolidinecarboxylic acids and salts thereof, plant extracts and vitamins;

cholesterol;

light stabilisers and UV absorbers as listed in Table below:

TABLE 1

UV absorbers which may be use in the dyeing compositions of the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4''-(1,3,5-triazine-2,4,6-triyltriimino)tris-tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxy-phenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo-[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |

TABLE 1-continued

UV absorbers which may be use in the dyeing compositions of the present invention

| No. | Chemical Name | CAS No. |
|---|---|---|
| 48 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

The use of UV absorbers can effectively protect natural and dyed hair from the damaging rays of the sun and increase the wash fastness of dyed hair.

Furthermore, the following UV absorbers or combinations may be used in the dyeing compositions according to the invention:

cationic benzotriazole UV absorbers as for example described in WO 01/36396 especially on p. 1, l. 20 to p. 2, l. 24, and preferred on p. 3 to 5, and on p. 26 to 37;

cationic benzotriazole UV in combination with antioxidants as described in WO 01/36396, especially on p. 11, l. 14 to p. 18;

UV absorbers in combination with antioxidants as described in U.S. Pat. No. 5,922,310, especially in col 2, l. 1 to 3;

UV absorbers in combination with antioxidants as described in U.S. Pat. No. 4,786,493, especially in col 1, 42 to col 2, l. 7, and preferred in col 3, 43 to col 5, l. 20;

combination of UV absorbers as described in U.S. Pat. No. 5,830,441, especially in col 4, l. 53 to 56;

combination of UV absorbers as described in WO 01/36396, especially on p. 11, l. 9 to 13; or triazine derivatives as described in WO 98/22447, especially on p. 1, l. 23 to p. 2, l. 4, and preferred on p. 2, l. 11 to p. 3, l. 15 and most preferred on p. 6 to 7, and 12 to 16.

Suitable cosmetic preparations may usually contain 0.05 to 40% b.w., preferably 0.1 to 20% b.w., based on the total weight of the composition, of one or more UV absorbers;

consistency regulators, such as sugar esters, polyol esters or polyol alkyl ethers;

fats and waxes, such as spermaceti, beeswax, montan wax, paraffins, fatty alcohols and fatty acid esters;

fatty alkanolamides;

polyethylene glycols and polypropylene glycols having a molecular weight from 150 to 50 000, for example such as those described in EP-A-801 942, especially p. 3, l. 44 to 55, complexing agents, such as EDTA, NTA and phosphonic acids, swelling and penetration substances, such as polyols and polyol ethers, as listed extensively, for example, in EP-A-962 219, especially p. 27, l. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;

opacifiers, such as latex;

pearlising agents, such as ethylene glycol mono- and di-stearate;

propellants, such as propane-butane mixtures, $N_2O$, dimethyl ether, $CO_2$ and air;

antioxidants; preferably the phenolic antioxidants and hindered nitroxyl compounds disclosed in ip.com (IPCOM # 000033153D);

sugar-containing polymers, as described in EP-A-970 687;

quaternary ammonium salts, as described in WO 00/10517;

Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% b.w., based on the solids content of the preparations;

The dyeing compositions according to the present invention generally comprise at least one surfactant.

Suitable surfactants are zwitterionic or ampholytic, or more preferably anionic, non-ionic and/or cationic surfactants.

Suitable anionic surfactants in the dyeing compositions according to the present invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having 10 to 22 carbon atoms (soaps), ether carboxylic acids of formula $R—O—(CH_2—CH_2—O)_x—CH_2—COOH$, in which R is a linear alkyl group having 10 to 22 carbon atoms and x=0 or from 1 to 16, acyl sarcosides having 10 to 18 carbon atoms in the acyl group, acyl taurides having 10 to 18 carbon atoms in the acyl group, acyl isothionates having 10 to 18 carbon atoms in the acyl group, sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups, linear alkane sulfonates having 12 to 18 carbon atoms,
linear α-olefin sulfonates having 12 to 18 carbon atoms,
α-sulfo fatty acid methyl esters of fatty acids having 12 to 18 carbon atoms,
alkyl sulfates and alkyl polyglycol ether sulfates of formula R'—O(CH$_2$—CH$_2$—O))$_{x'}$—SO$_3$H, in which R' is a preferably linearar alkyl group having 10 to 18 carbon atoms and x'=0 or from 1 to 12,
mixtures of surface-active hydroxysulfonates according to DE-A-3 725 030;
sulfated hydroxyalkylpolyethylene and/or hydroxyalkylenepropylene glycol ethers according to DE-A-3 723 354, especially p. 4, I. 42 to 62,
sulfonates of unsaturated fatty acids having 12 to 24 carbon atoms and 1 to 6 double bonds according to DE-A-3 926 344, especially p. 2, I. 36 to 54,
esters of tartaric acid and citric acid with alcohols which are addition products of approximately from 2 to 15 molecules of ethylene oxide and/or propylene oxide with fatty alcohols having from 8 to 22 carbon atoms, or
anionic surfactants, as described in WO 00/10518, especially p. 45, I. 11 to p. 48, I. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated C$_8$-C$_{22}$-carboxylic acids, such as oleic acid, stearic acid, isostearic acid and palmitic acid.

Surface-active compounds that carry at least one quaternary ammonium group and at least one —COO$^-$ or —SO$_3^-$ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazoline having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a C$_8$-C$_{18}$-alkyl or -acyl group and contain at least one free amino group and at least one —COOH or —SO$_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopro-pionate and C$_{12}$-C$_{18}$acylsarcosine.

Suitable non-ionic surfactants are described in WO 00/10519, especially p. 45, I. 11 to p. 50, I. 12. Non-ionic surfactants contain as hydrophilic group, for example, a polyol group, a poly-alkylene glycol ether group or a combination of polyol and polyglycol ether groups. Such compounds are, for example:

addition products of 2 to 30 mol of ethylene oxide and/or 0 to 5 mol of propylene oxide with linearar fatty alcohols having 8 to 22 carbon atoms, with fatty acids having 12 to 22 carbon atoms and with alkylphenols having 8 to 15 carbon atoms in the alkyl group, C$_{12}$-C$_{22}$ fatty acid mono- and di-esters of addition products of 1 to 30 mol of ethylene oxide with glycerol,
C$_8$-C$_{22}$alkyl-mono- and -oligo-glycosides and ethoxylated analogues thereof,
addition products of 5 to 60 mol of ethylene oxide with castor oil and hydrogenated castor oil,
addition products of ethylene oxide with sorbitan fatty acid esters,
addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethyl-lammonium chloride, lauryldimethylammonium chloride, lauryldimethylbenzylammonium chloride and tricetylmethyl-ammonium chloride. Further cationic surfactants that can be used in accordance with the invention are quaternised protein hydrolysates.

Also suitable are cationic silicone oils, such as, for example, the commercially available pro-ducts Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, I. 9 to p. 55, I. 2.

Alkylamidoamines, especially fatty acid amidoamines, such as the stearylamidopropyl-dimethylamine obtainable under the name Tego Amid® 18 are also preferred as surfactants in the present dyeing compositions. They are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat® 100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The dyes of formula (1) are suitable for the dyeing of organic material, preferably keratin-containing fibers.

A further preferred embodiment of the present invention relates to a method of treating keratin-containing fibers with a thiol dye of formula (1).

The process comprises
(a) contacting the keratin fiber with at least a compound of formula (1),
(b) leaving the fibers to stand, and
(c) then rinsing the fiber.

The process for dyeing is for example described in WO 01/66646 on page 15, line 32 to page 16, line 2.

A further preferred method comprises treating the hair in the presence of a reduction agent.

Preferred reduction agents are for example thioglycol acid or salts thereof, gycerine monothioglycolat, cystein, 2-mercaptopropionic acid, 2-mercaptoethylamine, thiolactic acid, thioglycerine, sodium sulfite, dithionithe, ammonium sulfite, sodium bisulfite, sodium metabisulfite, hydroquinone, phosphines, borhydride, cyanoborohydride, triacetoxy borohydride, trimethoxy borohydride salts (sodium, lithium, potassium, calcium auaternary salts).

Furthermore, the present invention relates to a process, comprising treating the hair with
(a) optionally a reduction agent,
(b) at least one single thiol dye of formula (1) as defined above, and
(c) with an oxidizing agent.

The step (a) may be of short duration from 0.1 sec to 30 minutes, for example from 0.1 seconds to 10 minutes with a reducing agent mentioned above.

The application of the dye mixture on the hair may be carried out at temperatures ranging from 15° to 100° C. Generally the application is carried out at room temperature.

The sequence of the reaction steps is generally not important, the reduction agent can be applied first or in a final step.

Usually, the oxidizing agent is applied together with an acid or a base.

The acid is for example citric acid, phosphoric acid or tartrate acid.

The base is for example sodium hydroxide, ammonia or monoethanolamine.

The dyes of formula (1) are suitable for all-over dyeing of the hair, that is to say when dyeing the hair on a first occasion, and also for re-dyeing subsequently, or dyeing of locks or parts of the hair.

The dyes of formula (1) are applied on the hair for example by massage with the hand, a comb, a brush, or a bottle, or a bottle, which is combined with a comb or a nozzle.

Further preferred is a process for dyeing keratin-containing fibers which comprises treating the keratin-containing fiber with at least one dye of formula (1), a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

Lightening the melanin has the advantageous effect of creating a unified dyeing in the case of grey hair, and, in the case of naturally pigmented hair, of bringing out the color, that is to say of making it more visible.

In general, the oxidizing agent containing composition is left on the fiber for 0, 1 sec to 15 minutes, in particular for 0.1 sec to 5 minutes at 15 to 45° C., usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations or enzymes are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

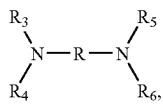

wherein
R is a propylene residue, which may be substituted with OH or $C_1$-$C_4$alkyl,
$R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations comprising the dyes of formula (1) on the keratin-containing fiber, preferably the hair is by using a multi-compartment dyeing device or "kit" or any other multi-compartment packaging system, as described for example in WO 97/20545 on p. 4, I. 19 to I. 27.

The first compartment contains for example at least one dye of formula (1) and optionally further direct dyes and a basifying agent, and in the second compartment an oxidizing agent; or in the first compartment at least one dye of formula (1) and optionally further direct dyes, in the second compartment a basifiying agent and in the third compartment an oxidizing agent.

A further preferred embodiment of the present invention relates to a method of dyeing hair with oxidative dyes, which comprises
(a) mixing at least one dye of formula (1) and optionally at least one coupler compound and at least one developer compound, and an oxidizing agent, which optionally contains at least one further dye, and (b) contacting the keratin-containing fibers with the mixture as prepared in step (a).

The pH-value of the oxidizing agent free composition is usually from 3 to 11, and in particular from 5 to 10, and most particular about 9 to 10.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)-alkylenediamines, and the acid-addition salts thereof, at least one coupler, especially selected from meta-phenylenediamines and the acid-addition salts thereof, and at least one dye of formula (1), on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis-(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one dye of formula (1), and, finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the dye(s) of formula (1) (themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminium oxides, kaolin, talc, silicates, mica and silicas.

A very suitable excipient in the dyeing compositions according to the invention is sawdust.

The powdered composition (A') may also contain binders or coating products in an amount which preferably does not exceed approximately 3% b.w. relative to the total weight of composition (A'). These binders are preferably selected from oils and liquid fatty substances of inorganic, synthetic, animal or plant origin.

Furthermore, the present invention relates to a process of dyeing of keratin-containing fibers of the dyes of formula (1) with autooxidable compounds and optionally further dyes.

Furthermore, the present invention relates to a process for dyeing keratin-containing fibers with the dyes of formula (1) and capped diazotised compounds, which comprises, (a) treating the keratin-containing fibers under alkaline conditions with at least one capped diazotised compound and a coupler compound, and optionally a developer compound ad optionally an oxidizing agent, and optionally in the presence of a further dye, and optionally with at least one dye of formula (1); and (b) adjusting the pH in the range of 6 to 2 by treatment with an acid, optionally in the presence of a further dye, and optionally at least one dye of formula (1), with the proviso that at least in one step (a) or (b) at least one dye of formula (1) is present.

The capped diazotised compound and coupler compound and optionally the oxidizing agent and developer compound can be applied in any desired order successively, or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are chieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

Furthermore, the present invention relates to a process for dyeing keratin-containing fibers with the dyes of formula (1) and at least one acid dye.

The following Examples serve to illustrate the processes for dyeing without limiting the processes thereto. Unless specified otherwise, parts and percentages relate to weight. The amounts of dye specified are relative to the material being coloured.

T, s, d, q and J, wherein t is a triplett, s is singulett, d is duplett, q is a quartett, and J is a coupling constant, define the NMR spectra values.

EXAMPLES

A. Preparation Examples

Example 1

Procedure (a)

Step 1: 6.34 g of 1-(3-methoxyphenyl)-piperazine dihydrochloride are suspended in 4 ml and cooled to 0-5° C.

8.58 g of a sodium methylate solution in methanol (1 mol methylate in 179.6 g solution) are added dropwise to this suspension, maintaining the temperature at 0-5° C.

After completion of the addition the mixture is was stirred for 30 min at room temperature. Finally the solvent is removed by evaporation and the remaining brown oil is dissolved in 40 ml dimethyl formamide.

6.58 g bis(2-(2-bromoacetamide) ethyl disulfide (RN 697755-79-6) and 4.66 g potassium carbonate are added to this solution and the reaction mixture is stirred for 5 days at 40° C. Then the reaction mass is poured into 50 ml diethyl ether.

The product precipitates as an oil, which is dissolved in 100 ml dichloromethane and washed with a NaHCO₃ solution.

The organic phase is dried over sodium sulphate and filtered.

Then the solvent is evaporated and the remaining oil is purified by column chromatography (acetone, silica) to obtain 0.64 g of compound of formula

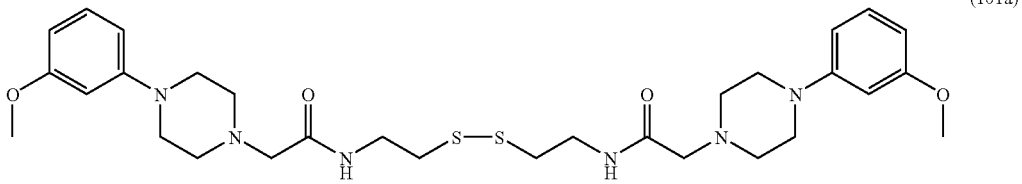

(101a)

MS (ES+): m/z 617 (M+1).

Step 2: 0.88 g HBr (33%) are added drop wise to a suspension of 0.5 g of the compound of formula (1o1a) in 2 g dimethyl formamide and 2.5 g water at 0-5° C.

After completion of the addition the yellow solution is warmed up to room temperature and 0.32 g of an aqueous sodium nitrite solution (46 w. %) is added slowly.

The reaction mixture is stirred at room temperature until the test on nitrite is negative (potassium iodide/starch paper).

The dark reaction mixture is used for reaction step 3.

Step 3: 0.27 g 3-diethylaminophenol are dissolved in 3 g dimethyl formamide and after addition of a few drops of HBr (33%) the solution is heated to 70° C.

At this temperature the dark reaction mixture obtained in the nitrosation step is added via a dropping funnel over a period of 1 h.

The resulting blue solution is stirred for an additional hour, then cooled to room temperature and poured into 200 ml of acetone.

The precipitate is collected by filtration and dried in vacuo to obtain 0.43 g of the compound of formula (101)

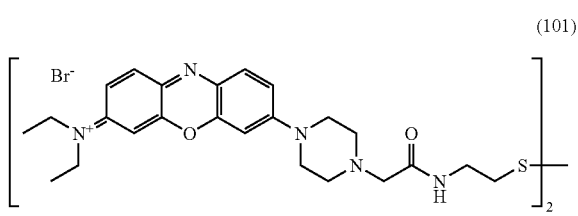

(101)

as a dark blue powder, which can be used for the dyeing of hair.

MS (ES+): m/z 453 (M²⁺); UV/VIS (water): $\lambda_{max1}$ 642 nm, $\lambda_{max2}$ 588 nm.

Example 2

Procedure (b)

Step 1: A solution of 7.58 g of 3-diethylamino-anisole in 37 g dimethyl formamide and 45 g water is cooled to 0° C. Then 19.5 g HBr (33%) are added via a dropping funnel over a period of 1 h, during which time the temperature is rising to 15° C.

Then 7.04 g of an aqueous sodium nitrite solution (46 w. %) is added dropwise over a period of 30 min.

The reaction mixture is stirred at room temperature until the test on nitrite is negative (potassium iodide/starch paper).

The resulting dark solution is used for step 2.

Step 2: A solution of 6.68 g 1-(3-hydroxyphenyl)piperazine and 9 g HBr (33%) in 10 g dimethyl formamide is heated to 70° C.

At this temperature the dark solution obtained in step 1 s added via a dropping funnel over a period of 2.5 h.

The resulting blue solution ios stirred for an additional hour, then cooled to room temperature and poured into 300 ml of acetone.

The precipitate is collected by filtration and stirred in 100 ml of refluxing acetone two times before it is filtered off and dried in vacuo to obtain 6.97 g of the compound of formula

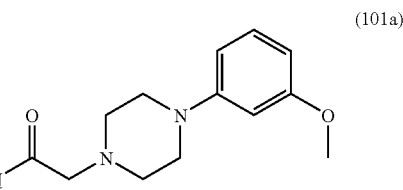

(102a)

as a dark blue powder, which is used for step 3.

MS (ES+): m/z 337 (M⁺−1); UV/VIS (water): $\lambda_{max1}$ 634 nm, $\lambda_{max2}$ 590 nm.

Step 3: A solution of 0.5 g of the compound of formula (102a), 0.24 g of bis(2-(2-bromo-acetamide)ethyl)-disulfide (RN 697755-79-6) and 0.08 g of potassium carbonate in 50 ml methanol is stirred at 40° C. for 12 h.

After that time the solvent is removed by evaporation, the remaining solid is dissolved in 5 ml dimethyl formamide and this solution is dropped into 20 ml of acetone.

The resulting precipitate is collected by filtration and dried to obtain 0.23 g of the compound of formula (101) as a dark blue powder, which can be used for the dyeing of hair.

MS (ES+): m/z 453 (M²⁺); UV/VIS (water): $\lambda_{max1}$ 642 nm, $\lambda_{max2}$ 588 nm.

B. Application Examples

The washing fastness of the dyed hair is analyzed by the Grey scale according to Industrial organic pigments by Herbst & Hunger, 2nd ed. engl. S. 61) Nr 10: DIN 54 001-8-1982, "Herstellung und Bewertung der Aenderung der Farbe", ISO 105-A02-1993.

In the following application examples compositions within the below given definitions are used:

Solution 1 (permanent lotion, pH 8.2):

Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Parfum Solution 2 (permanent fixation, pH 3.9):
Based on:
Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, Coco-Betaine, Acetaminophen, Phosphoric Acid, Sodium Chloride, Parfum Solution 3 (dyeing solution):
0.1% of the dye is dissolved in a 10% solution of a non-ionic surfactant (Plantacare 200UP, Henkel) adjusted to pH 9.5 using citric acid or monoethanolamine.

Application Example B1

0.1%, by weight coloring material solution consisting of the compound of formula (2) in water (pH 9.5) is applied on the dry hair (two blond, two middle blond, two brown and two damaged hair strands) and allowed to stand for 20 min. at room temperature. Then, the strands are rinsed under tap water and dried 12 hours.
Washing fastness: 10× washed with shampoo.

Results:

| Strand | Colour result | Washing fastness |
|---|---|---|
| blond | blue/good | 4-5 |
| middle blond | green/good | 4 |
| damaged | blue/good | 4 |

Application Example B2

A solution 1 (permanent lotion) is applied on shampooed hair (two blond, two middle blond, two brown and two damaged hair strands) and allowed to stand for 10 min. Then, the strands are rinsed under tap water, and the towel dry strands are treated with the 0.1%, by weight colouring material solution of example B1 allowed to stand for 20 min and then rinsed. Then, the towel dry strands are treated with the solution 2 (permanent fixation) and allowed to stand for 10 min. Then the strands are rinsed under tap water and dried 12 hours at room temperature.
Washing fastness: 10× washed with shampoo.

Results:

| Strand | Colour | Washing fastness |
|---|---|---|
| blond | blue/good | 5 |
| middle blond | green/good | 5 |
| damaged | blue/good | 5 |

The invention claimed is:

1. Compounds of formula (1)

$$D_1\text{-}(Z_1)_r\text{-}Y_1\text{---}S\text{-}A \quad (1),$$

wherein
A is hydrogen; or a radical of formula (1a) *—S—$Y_2$—$(Z_2)_r$-$D_2$;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—$(CH_2)_p$—C(O)—**; *—$(CH_2CH_2$—O$)_s$—**; *—$(CH_2)_p$—C(O)O—**; *—$(CH_2)_p$—OCO—**; *—$(CH_2)_p$—N($R_1$)—**;

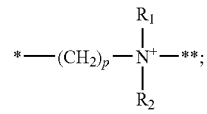

*—$(CH_2)_p$—CON($R_1$)—**; *—$(CH_2)_p$—($R_1$)NC(O)—**; O—; S—; —S(O)—; —S(O)$_2$—; or a cationic biradical of a substituted or unsubstituted aromatic or heteroaromatic compound of the formula

(1a)

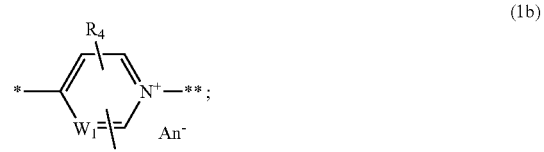

(1b)

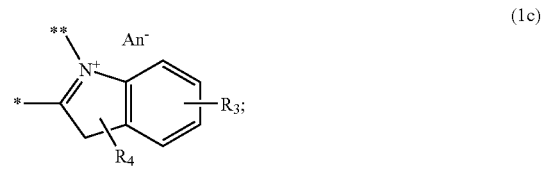

(1c)

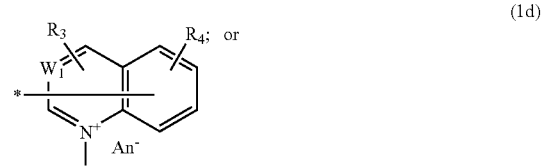

(1d)

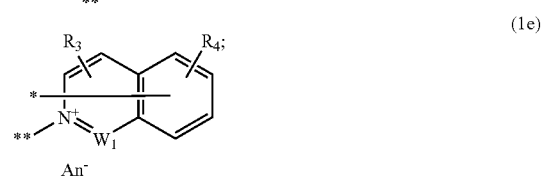

(1e)

wherein
the asterix * indicates the linkage to $D_1$ and/or $D_2$;
the asterix ** indicates the linkage to $Y_1$ and/or $Y_2$;
$W_1$ is N or a radical of $CR_5$;
$R_1$, $R_2$, $R_3$, $R_4$ and $R_5$ independently from each other are hydrogen; $C_1$-$C_{14}$alkyl; $C_2$-$C_{14}$alkenyl; $C_5$-$C_{10}$aryl; $C_5$-$C_{10}$aryl-($C_1$-$C_{10}$alkyl); or —$C_1$-$C_{10}$alkyl($C_5$-$C_{10}$aryl);
$D_1$ and $D_2$ independently from each other ar the residue of an organic dye selected from the radical of formula

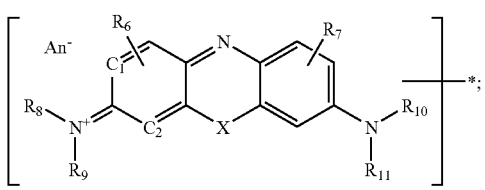
(1f)

$R_6$ and $R_7$ independently from each other are hydrogen; $C_1$-$C_{20}$alkyl; $C_1$-$C_{20}$alkoxy; $C_3$-$C_6$cycloalkyl; $C_5$-$C_{10}$aryl; anellated aromatic groups; carboxylate; or sulfonate groups;

$R_8$, $R_9$ and $R_{10}$, $R_{11}$ and $R_{12}$ each independently from each other are hydrogen; unsubstituted or substituted, straight-chain or branched, monocyclic or polycyclic, interrupted or uninterrupted $C_1$-$C_{14}$alkyl, $C_2$-$C_{14}$alkenyl, $C_6$-$C_{10}$aryl, $C_6$-$C_{10}$aryl-$C_1$-$C_{10}$alkyl or $C_5$-$C_{10}$alkyl($C_5$-$C_{10}$aryl); or $R_8$ and $R_9$ or $R_{10}$ and $R_{11}$ together with the linking nitrogen atom form a 5 to 7 membered carbocyclic ring which may contain one or more than one hetero atom; or $R_8$ is linked to $C_1$ together with $N^+$ forming a 5-7 membered carbocyclic ring; or $R_9$ is linked to $C_2$ together with $N^+$ forming a 5-7 membered carbocyclic ring;

X is —O—; or —N($R_9$)—; or —S—;

p is a number from 0 to 5;

r is 0 or 1; and s is a number from 1 to 5.

2. Compounds according to claim 1, wherein $Y_1$ and $Y_2$ are $C_5$-$C_{10}$cycloalkylene; or $C_1$-$C_{10}$alkylene.

3. Compounds according to claim 1, wherein $Y_1$ and $Y_2$ are $C_1$-$C_5$alkylene.

4. Compounds according to claim 1, wherein $Z_1$ and $Z_2$ independently from each other are —CO—; *—CH$_2$—CO—NH—**; *—(CH$_2$)$_3$—N$^+$(CH$_3$)(CH$_3$)—; or —(CO)—O—*.

5. Compounds according to claim 1, wherein in formula (1f)

$R_7$ and $R_8$ or $R_9$ and $R_{10}$ together with the linking nitrogen atom form a piperidine ring of formula

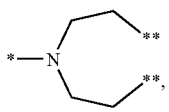
(1b)

wherein the asterix(*) is directed to $Z_1$ or $Z_2$ respectively; and the asterices (**) are directed to the linking nitrogen atom of $R_7$/$R_8$ or $R_9$/$R_{10}$ respectively.

6. Compounds according to claim 1, wherein n is 2.

7. Compounds according to claim 1, wherein $D_1$ is identical to $D_2$;

$Y_1$ is identical to $Y_2$;

$Z_1$ is identical to $Z_2$;

p is 0; or 1; and r is 1.

8. A method of dyeing keratin-containing fibers comprising treating the fiber with at least one compound of formula (1)

$$D_1\text{-}(Z_1)_r\text{—}Y_1\text{—}S\text{-}A \qquad (1),$$

wherein

A is hydrogen; or a radical of formula (1a) *—S—$Y_2$—$(Z_2)_r$-$D_2$;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—(CH$_2$)$_p$—C(O)—**; *—(CH$_2$CH$_2$—O)$_s$—**; *—(CH$_2$)$_p$—C(O)O—**; *—(CH$_2$)$_p$—OCO—**; *—(CH$_2$)$_p$—N(R$_1$)—**;

$$*\text{—}(CH_2)_p\text{—}\overset{R_1}{\underset{R_2}{N^+}}\text{—}**;$$

*—(CH$_2$)$_p$—CON(R$_1$)—**; *—(CH$_2$)$_p$—(R$_1$)NC(O)—**; *O—; —S—; —S(O)—; —S(O)$_2$—; or a cationic biradical of a substituted or unsubstituted aromatic or heteroaromatic compound of the formula

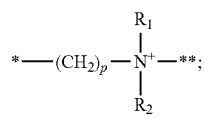
(1a)

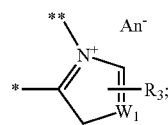
(1b)

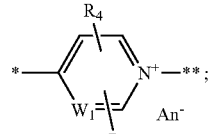
(1c)

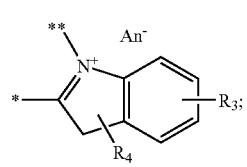
(1d)

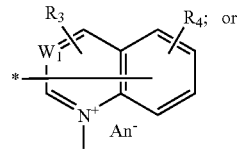
(1e)

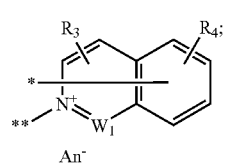

wherein the asterix * indicates the linkage to $D_1$ and/or $D_2$;

the asterix ** indicates the linkage to $Y_1$ and/or $Y_2$;

$W_1$ is N or a radical of CR$_5$;

$R_1$, $R_2$, $R_3$, $R_4$ and $R_5$ independently from each other are hydrogen; $C_1$-$C_{14}$alkyl; $C_2$-$C_{14}$alkenyl; $C_5$-$C_{10}$aryl; $C_5$-$C_{10}$aryl-($C_1$-$C_{10}$alkyl); or —$C_1$-$C_{10}$alkyl($C_5$-$C_{10}$aryl);

$D_1$ and $D_2$ independently from each other ar the residue of an organic dye selected from the radical of formula

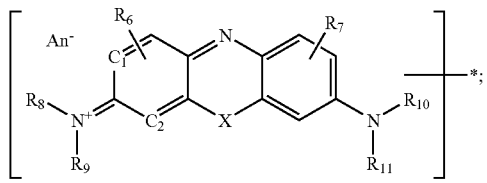

(1f)

$R_6$ and $R_7$ independently from each other are hydrogen; $C_1$-$C_{20}$alkyl; $C_1$-$C_{20}$alkoxy; $C_3$-$C_6$cycloalkyl; $C_5$-$C_{10}$aryl; anellated aromatic groups; carboxylate; or sulfonate groups;

$R_8$, $R_9$ and $R_{10}$, $R_{11}$ and $R_{12}$, each independently from each other are hydrogen; unsubstituted or substituted, straight-chain or branched, monocyclic or polycyclic, interrupted or uninterrupted $C_1$-$C_{14}$alkyl, $C_2$-$C_{14}$alkenyl, $C_6$-$C_{10}$aryl, $C_6$-$C_{10}$aryl-$C_1$-$C_{10}$alkyl or $C_5$-$C_{10}$alkyl($C_5$-$C_{10}$aryl); or $R_8$ and $R_9$ or $R_{10}$ and $R_{11}$ together with the linking nitrogen atom form a 5 to 7 membered carbocyclic ring which may contain one or more than one hetero atom; or $R_8$ is linked to $C_1$ together with $N^+$ forming a 5-7 membered carbocyclic ring; or $R_9$ is linked to $C_2$ together with $N^+$ forming a 5-7 membered carbocyclic ring;

X is —O—; or —N($R_9$)—; or —S—;

p is a number from 0 to 5;

r is 0 or 1; and s is a number from 1 to 5.

9. A method according to claim 8, wherein the dyeing is carried out in presence of a reducing agent.

10. A method according to claim 9, wherein the reducing agent is selected from the group consisting of thioglycol acid or salts thereof, gycerine monothioglycolate, cystein, 2-mercaptopropionic acid, 2-mercaptoethylamine, thiolactic acid, thioglycerine, sodium sulfite, dithionithe, ammonium sulfite, sodium bisulfite, sodium metabisulfite and hydrochinon.

11. A method according to claim 8, comprising treating the keratin-containing fiber (a) optionally with a reduction agent, and (b) with at least one single dye of formula (1), and (c) optionally with an oxidizing agent.

12. A composition comprising at least one compound of formula (1)

$$D_1\text{-}(Z_1)_r\text{-}Y_1\text{-}S\text{-}A \quad (1),$$

wherein

A is hydrogen; or a radical of formula (1a) *—S—$Y_2$—$(Z_2)_r$-$D_2$;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—(CH$_2$)$_p$—C(O)—**; *—(CH$_2$CH$_2$—O)$_s$—**; *—(CH$_2$)$_p$—C(O)O—**; *—(CH$_2$)$_p$—OCO—**; *—(CH$_2$)$_p$—N(R$_1$)—**;

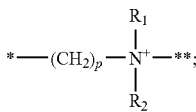

*—(CH$_2$)$_p$—CON(R$_1$)—**; *—(CH$_2$)$_p$—(R$_1$)NC(O)—**; *O—; —S—; —S(O)—; —S(O)$_2$—; or a cationic biradical of a substituted or unsubstituted aromatic or heteroaromatic compound of the formula

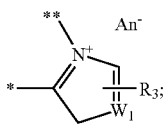

(1a)

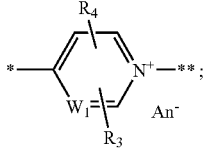

(1b)

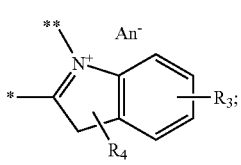

(1c)

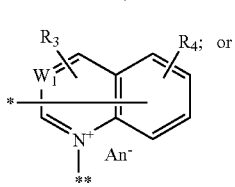

(1d)

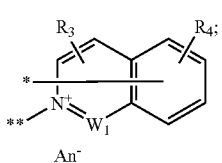

(1e)

wherein the asterix * indicates the linkage to $D_1$ and/or $D_2$;

the asterix ** indicates the linkage to $Y_1$ and/or $Y_2$;

$W_1$ is N or a radical of $CR_5$;

$R_1$, $R_2$, $R_3$, $R_4$ and $R_5$ independently from each other are hydrogen; $C_1$-$C_{14}$alkyl; $C_2$-$C_{14}$alkenyl; $C_5$-$C_{10}$aryl; $C_5$-$C_{10}$aryl-($C_1$-$C_{10}$alkyl); or —$C_1$-$C_{10}$alkyl($C_5$-$C_{10}$aryl);

$D_1$ and $D_2$ independently from each other ar the residue of an organic dye selected from the radical of formula (1f)

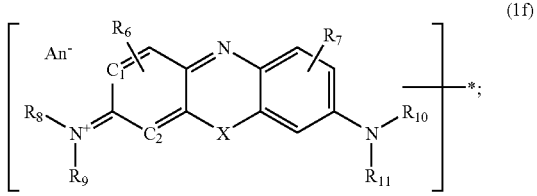

(1f)

$R_6$ and $R_7$ independently from each other are hydrogen; $C_1$-$C_{20}$alkyl; $C_1$-$C_{20}$alkoxy; $C_3$-$C_6$cycloalkyl; $C_5$-$C_{10}$aryl; anellated aromatic groups; carboxylate; or sulfonate groups;

$R_8$, $R_9$ and $R_{10}$, $R_{11}$ and $R_{12}$ each independently from each other are hydrogen; unsubstituted or substituted, straight-chain or branched, monocyclic or polycyclic, interrupted or uninterrupted $C_1$-$C_{14}$alkyl, $C_2$-$C_{14}$alkenyl, $C_6$-$C_{10}$aryl, $C_6$-$C_{10}$aryl-$C_1$-$C_{10}$alkyl or $C_5$-$C_{10}$alkyl($C_5$-$C_{10}$aryl); or $R_8$ and $R_9$ or $R_{10}$ and $R_{11}$ together with the linking nitrogen atom form a 5 to 7 membered carbocyclic ring which may contain one or more than one hetero atom; or $R_8$ is linked to $C_1$ together with $N^+$ forming a 5-7 membered carbocyclic ring; or $R_9$ is linked to $C_2$ together with $N^+$ forming a 5-7 membered carbocyclic ring;

X is —O—; or —N($R_9$)—; or —S—;

p is a number from 0 to 5;

r is 0 or 1; and s is a number from 1 to 5.

13. A composition according to claim 12 in form of a shampoo, conditioner, gel or emulsion.

14. A composition according to claim 12 comprising at least one single compound of formula (1), and a direct dye and/or a reactive dye.

* * * * *